United States Patent

Falk

[11] Patent Number: 4,485,251
[45] Date of Patent: Nov. 27, 1984

[54] PROCESS FOR THE PREPARATION OF BIS(PERFLUOROALKYL-ALKYLTHIO)ALKANOIC ACIDS AND LACTONE INTERMEDIATES THEREOF

[75] Inventor: Robert A. Falk, New City, N.Y.

[73] Assignee: Ciba-Geigy Corporation, Ardsley, N.Y.

[21] Appl. No.: 452,531

[22] Filed: Dec. 23, 1982

[51] Int. Cl.$^3$ ............................................ C07D 307/32
[52] U.S. Cl. ........................................................ 549/513
[58] Field of Search ............................................ 549/313

[56] References Cited

U.S. PATENT DOCUMENTS 4,239,915 12/1980 Falk ...................................... 562/481
4,419,298 12/1983 Falk et al. .......................... 260/501.16

Primary Examiner—Norma S. Milestone
Attorney, Agent, or Firm—Michael W. Glynn

[57] ABSTRACT

Disclosed is a process for the preparation of a bis(perfluoroalkyl-alkylthio)alkanoic acid of the formula

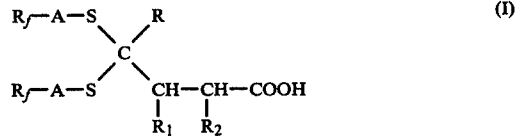

wherein
each $R_f$ is independently perfluoroalkyl of 3 to 18 carbon atoms or perfluoroalkoxyperfluoroalkyl of 3 to 18 carbon atoms, or mixtures thereof;
each A is independently alkylene of up to 6 carbon atoms or said alkylene interrupted by —O—; N(H)— or —N(lower alkyl)—;

R is hydrogen or alkyl of 1 to 6 carbon atoms;
$R_1$ is hydrogen or lower alkyl; and
$R_2$ is hydrogen, lower alkyl, aryl or aryl substituted lower alkyl;

by reacting a perfluoroalkyl-alkyl mercaptan of the formula

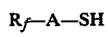 (II)

with a lactone of the formula

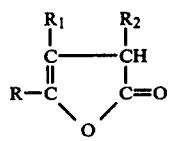 (III)

in the presence of a catalytic amount of a Lewis acid to form a perfluoroalkyl-alkylthio lactone of the formula

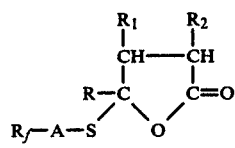 (IV)

and reacting said perfluoroalkyl-alkylthio lactone with additional perfluoroalkyl-alkylmercaptan of the formula

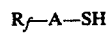 (IIa)

in the presence of a catalytic amount of a Lewis acid, to obtain said bis(perfluoroalkyl-alkylthio)alkanoic acid of formula (I).

5 Claims, No Drawings

PROCESS FOR THE PREPARATION OF BIS(PERFLUOROALKYL-ALKYLTHIO)ALKANOIC ACIDS AND LACTONE INTERMEDIATES THEREOF

GENERAL DESCRIPTION OF THE INVENTION

Bis(perfluoroalkyl-alkylthio)alkanoic acids of the formula

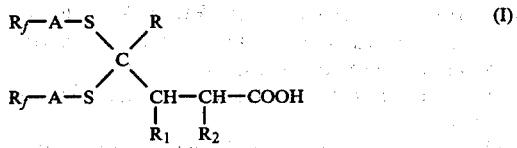

wherein each $R_f$ is independently perfluoroalkyl of 3 to 18 carbon atoms or perfluoroalkoxyperfluoroalkyl of 3 to 18 carbon atoms, or mixtures thereof;

each A is independently alkylene of up to 6 carbon atoms or said alkylene interrupted by —O—, —N(H)— or —N(lower alkyl)—;

$R_1$ is hydrogen or lower alkyl;

$R_2$ is hydrogen, lower alkyl, aryl or aryl substituted lower alkyl; and

R is hydrogen or alkyl of 1 to 6 carbon atoms, have been found to be highly advantageous in the form of the ammonium and amine salts thereof, especially the alkanolamine salts, such as the diethanolamine salt thereof forms aqueous solutions and emulsions which are useful in rendering natural and synthetic polyamide materials, such as leather and polyamide textile materials, and cellulosic materials, such as paper articles, hydrophobic and oleophobic.

It is an object of the instant invention to provide a new process for the preparation of such bis(perfluoroalkylalkylthio)alkanoic acids.

It is a further object of the instant invention to provide the artisan with novel perfluoroalkyl-alkylthio lactone intermediates. These and other objects of the invention are apparent from the following detailed description.

DETAILED DESCRIPTION OF THE INVENTION

One object of the instant invention is a process for the preparation of bis(perfluoroalkyl-alkylthio) alkanoic acids of the formula

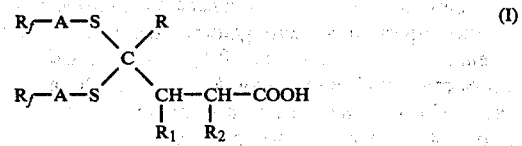

wherein each $R_f$ is independently perfluoroalkyl of 3 to 18 carbon atoms or perfluoroalkoxyperfluoroalkyl of 3 to 18 carbon atoms, or mixtures thereof;

each A is independently alkylene of 1 to 6 carbon atoms, alkyleneoxyalkylene of up to 6 carbon atoms, alkylene —NH-alkylene of up to 6 carbon atoms or alkylene-N(lower alkyl)-alkylene, where the alkylene groups have a total of up to 6 carbon atoms;

R is hydrogen or lower alkyl;

$R_1$ is hydrogen or lower alkyl; and $R_2$ is hydrogen, lower alkyl, aryl or aryl substituted lower alkyl;

by reacting a perfluoroalkyl-alkylmercaptan of the formula $$R_f{-}A{-}SH \qquad (II)$$

wherein $R_f$ and A are as defined above, with a lactone of the formula

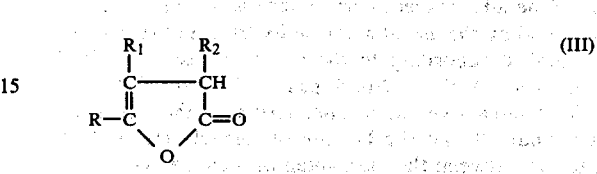

where R, $R_1$ and $R_2$ are as defined above, in the presence of a catalytic amount of a Lewis acid, to form a perfluoroalkyl-alkylthio lactone of the formula

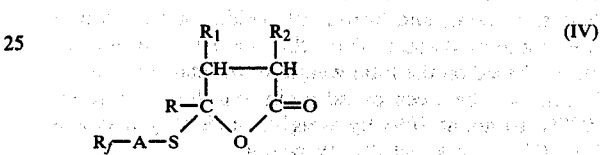

wherein $R_f$, A, R, $R_1$ and $R_2$ are as defined above, and reacting said perfluoroalkyl-alkylthio lactone, with or without isolation thereof, with additional perfluoroalkyl-alkylmercaptan of the formula $$R_f{-}A{-}SH \qquad (IIa)$$

wherein $R_f$ and A are as defined above, in the presence of a catalytic amount of a Lewis acid, to obtain the bis(perfluoroalkyl-alkylthio)alkanoic acid of formula I.

The $R_f$ group may be straight or branched chain.

By "lower" in regard to organic moieties is meant those having 1 to 6 carbon atoms.

Preferably $R_f$ is perfluoroalkyl of 4 to 16 carbon atoms. Advantageously, the $R_f$ group may be a mixture of such perfluoroalkyl groups.

By "aryl" there is advantageously included phenyl or phenyl substituted by lower alkyl, lower alkoxy, halo, especially chloro or bromo, lower alkanoyl and lower alkanoyloxy. Preferred aryl includes phenyl, tolyl, methoxyphenyl and dimethoxyphenyl. Preferred aryl substituted lower alkyl includes phenyethyl and especially benzyl.

A is preferably alkylene of 2 to 4 carbon atoms, and is most preferably ethylene, i.e. —$CH_2CH_2$—.

R is preferably hydrogen or alkyl of 1 to 4 carbon atoms, and is most preferably methyl.

$R_1$ is preferably hydrogen or methyl, and most preferably hydrogen.

$R_2$ is preferably hydrogen, methyl, ethyl or benzyl, and most preferably hydrogen.

The lactones of formula III belong to a known class of compounds, and many have been prepared by the dehydration of the corresponding keto acids, viz.:

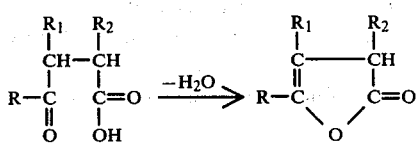

by a variety of techniques, including slow dehydration, or by dehydration in the presence of an acidic dehydrating agent, such as $H_3PO_4$, acetyl chloride, acetic anhydride-sulfuric acid mixtures, acetic anhydride, and the like. One advantageous procedure is to dehydrate the keto acid by the use of acetic anhydride and Amberlyst 15 catalyst according to the procedure set forth in *J. Het. Chem.*, Vol. 12, No. 4, pages 749–754 (1975).

As stated above, the reactions between the mercaptan of formula II and the lactone of formula III, and the reaction between the mercaptan of formula IIa and the substituted lactone of formula IV, are advantageously conducted in the presence of a catalytic amount of a Lewis acid. Suitable Lewis acids include the mineral acids, such as HCl and $H_2SO_4$, organic acids such as acetic acid, para toluene sulfonic acid and the like, acid clays and resins, and boron trifluoride, or the diethyl ether complex thereof. Thus, the amount by weight of catalyst based on the total weight of the starting materials can vary between broad limits, e.g. between about 0.005% to about 10% by weight, preferably between about 0.01% to about 2% by weight.

Moreover, representative lactones of formula III and alternate synthetic methods for their preparation e.g. from beta, gamma dibromo acids, substituted propargylmalonic acids, and the like, are known in the art, as see Y. Shyamsunder Rao, *Chem. Rev.*, Vol. 46, No. 4, pages 353–388 (1964).

The perfluoroalkyl-alkyl mercaptans of formula II and IIa may be the same or different and commercially available conventional mixtures of perfluoroalkyl-alkyl mercaptans may be used.

In one embodiment, the perfluoroalkyl-alkylthio lactone of formula IV may be isolated. If it is desired to isolate the compound of formula IV, the mole ratio of the mercaptan of the formula II to the lactone of formula III is desirably between about 0.1–1.2:1, preferably between about 0.5–1:1.

The perfluoroalkyl-alkylthio lactone of formula IV may be then separated from the reaction mixture by conventional techniques, such as precipitation and filtration. For example, if the reaction is conducted in the presence of an inert solvent, such as benzene, toluene, chlorobenzene, methoxybenzene or the like, the reaction mixture may be cooled, and optionally a substantial non solvent for the compound of formula IV, such as an alkane, e.g. heptane added, to promote precipitation. The precipitated compound of formula IV may then be isolated by separation from the liquid mixture, such as by filtration, decantation, and the like.

In an alternate embodiment, the perfluoroalkyl-alkylthio lactone of formula IV need not be isolated, but is further reacted by the addition of the perfluoroalkyl-alkyl mercaptan of formula IIa. Desirably, sufficient additional perfluoroalkylalkyl mercaptan of formula IIa is added such that the total mole ratio of mercaptan (formula II plus IIa) added to the reaction mixture based on the amount of the lactone of formula III is between about 1.3–2.4:1, preferably about 1.6–2.2:1, to obtain the product of formula I.

In another alternate embodiment, where it is not desired to isolate the perfluoroalkyl-alkylthio lactone of formula IV, then the reaction to obtain the product of formula I may be conducted in one step, by the addition of the requisite mole ratio of mercaptan to lactone as set forth in the preceeding paragraph.

The reaction temperature for the process, whether conducted in two steps, or in one step, can be between about −20° C. and 120° C., preferably between about 0° C. and 60° C.

The reactions between the compounds of formula II and formula III, and formula IV and formula IIa, respectively, are advantageously conducted in a substantially liquid phase, i.e. as a suspension or solution, irrespective of whether the process is conducted in one or two steps.

Thus, where one or more of the starting materials are liquid, under the reaction conditions the reaction may be conducted in the presence or absence of an inert liquid solvent or diluent. Where all of the starting materials are solid and do not form a liquid eutectic mixture under the reaction conditions, an inert solvent or diluent is advantageously employed. The nature of the solvent or diluent is not critical, but should not interfere with the desired reaction. Suitable solvents and diluents include aliphatic and aromatic hydrocarbons which are unsubstituted or substituted with non-reactive substituents, such as benzene, toluene, chlorobenzene, dichlorobenzene, methoxybenzene, methylene chloride, xylene, decane, dipropyl ether, acetic acid, and the like. In order to assist in driving the reaction to completion, it is additionally contemplated to use a solvent wherein the desired final product, e.g. the product of formula I, is substantially less soluble or insoluble in the reaction medium and wherein the starting materials are relatively more soluble, such as toluene, ethyl benzene, hexane, and the like.

The following Examples are set forth for illustrative purposes only and are not intended to limit the scope of the invention. All parts are by weight unless otherwise stated.

EXAMPLE 1

4-hydroxy-4-[2-(n-heptadecafluorooctyl)ethylthio]-pentanoic acid acid gamma-lactone

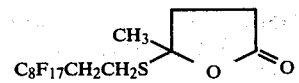

15 Grams (0.15 mol) of alpha-angelicalactone (4-hydroxy-3-pentenoic acid gamma-lactone), 250 ml of toluene, and 48 grams of (0.1 mol) of of 2-(n-perfluorooctyl)ethyl mercaptan are added to a reaction vessel. There is then added a small amount (about 0.5 grams) of p-toluene sulfonic acid, and the solution is stirred for about 16 hours at ambient temperature. The mixture is cooled to 0° C., stirred for 1 hour and filtered cold. The resulting precipitate is then washed with a small amount of cold toluene (about 10 ml) and dried in a partial vacuum at 40° C. 34 grams of 4-hydroxy-4-[2-(n-heptadecafluorooctyl)ethylthio]-pentanoic acid gamma-lactone are obtained in 96% purity by gas-liquid chromatography.

Analysis for $C_{15}H_{11}F_{17}O_2S$: Found: C, 30.6; H, 1.9; F, 53.0; S, 5.6 Calc: C, 31.2; H, 1.9; F, 55.9; S, 5.6.

The mass spectrum was consistent with the structure of the product. The molecular ion was not present, but ions of m/z 534 (—$CO_2$) and m/z 99 (—$C_8F_{17}CH_2CH_2S$) were observed.

EXAMPLE 2

4,4-Bis-[2-(n-perfluoroalkyl)ethylthio]-pentanoic acid
$R_fCH_2CH_2S)_2C(CH_3)CH_2CH_2COOH$ 5.0 Grams (0.05 mol), of alpha-angelicalactone (4-hydroxy-3-pentenoic acid gamma-lactone), 140 ml of toluene, 55.6 grams grams (0.1 mol) of 2-(n-perfluoroalkyl)ethyl mercaptan of the formula $R_f$—$CH_2CH_2SH$, wherein present $R_f$ is $C_6/C_8/C_{10}/C_{12}/C_{14}=3/29/47/17/3$, is charged into a 500 ml reaction vessel and heated to 40° C. Then, approximately 0.5 ml of boron trifluoride etherate 1:1 complex is added and the reaction mixture is stirred for two hours under a nitrogen atmosphere blanket while maintaining a reaction temperature of 40°–45° C. The reaction mixture is then cooled to 0°–5° C. and stirred for one hour. The product, 4,4-bis-[2-(n-perfluoroalkyl)ethylthio]-pentanoic acid is obtained as a suspension with a conversion of 90%. The product is isolated from solution by adding about 50 ml. of n-heptane at about 0° C., and recovering the product precipitate by filtration. It is a white solid of m.p. 112°–115°.

EXAMPLE 3

4,4-Bis-[2-(n-perfluorooctyl)ethylthio]-pentanoic acid
$(C_8F_{17}CH_2CH_2S)_2C(CH_3)CH_2CH_2COOH$ 5.0 Grams (0.05 mol) of alpha-angelicalactone, 27.8 grams (0.05 ml) of 2-(n-perfluorooctyl)ethyl mercaptan, 80 ml of toluene and 0.5 grams of p-toluene sulfonic acid are charged under nitrogen to a reaction vessel. The reaction mixture is stirred for about 16 hours at approximately 25° C. A white suspension of 4-hydroxy-4-[2-(n-perfluorooctyl)ethylthio]-pentanoic acid gamma-lactone is obtained in 80–90% conversion. Then an additional 27.8 grams (0.05 mol) of 2-(n-perfluorooctyl)ethyl mercaptan, 70 ml toluene and 0.5 grams of boron trifluoride etherate is added to the reaction mixture suspension. The resulting mixture is stirred at a temperature of 40°–45° C. for two hours. After cooling to 0° C. and stirring for a hour at ambient temperature the resulting white suspension is filtered and washed with toluene. The precipitate is then dried under reduced pressure at 40° C. The 4,4-bis-[2-(n-perfluorooctyl)ethylthio]-pentanoic acid product is 99% pure by gas-liquid chromatography.

It is a white powder of m.p. 106° with an nmr consistent with its structures.

EXAMPLE 4

4,4-Bis-[2-(n-perfluorobutyl)ethylthio]-pentanoic acid
$(C_4F_9CH_2CH_2S)_2C(CH_3)CH_2CH_2COOH$ 2.1 Grams (0.021 mol) of alpha-angelicalactone, 11.2 grams of 2-(n-perfluorobutyl)ethyl mercaptan (0.04 mol), 30 ml. toluene and about 0.5 ml of boron trifluoride etherate 1:1 complex, is charged into a reaction vessel at ambient temperature (approx. 20° C.), which is followed by a slight exotherm to about 29° C. After about 22 hours at room temperature (approx. 20° C.) the solution is diluted with about 30 ml. n-heptane and is cooled to about 0° C. The resulting suspension is filtered and the precipitate is washed with heptane and dried in a vacuum. The resulting product, 4,4-bis-[2-(n-perfluorobutyl)ethylthio]-pentanoic acid is obtained in 86% purity, as confirmed by NMR analysis. Assignments: 1.58, s $\underline{CH_3}$; 1.77–3.33, br.complex 12 protons $\underline{CH_2}$; 10.90, s. exchangeable: proton $\underline{OH}$.

It has a melting point of 65° C.

USING THE METHODS DESCRIBED AND BY THE TECHNIQUES ANALOGOUS TO EXAMPLES 1–4, THE FOLLOWING LACTONES AND ACIDS ARE PREPARED
EXAMPLE 5

| Mercaptan II | Mercaptan IIa | Lactone III | Perfluorolactone IV | Bisperfluoro-alkanoic acid I |
|---|---|---|---|---|
| 5. $(CF_3)_2CFOCF_2CH_2CH_2SH$ | $(CF_3)_2CFOCF_2CH_2CH_2SH$ | (structure with CH₃, CH—CH, CH, C=O, O, CH₃) | (structure with CH₃, CH₂—CH, CH₂, C=O, O, CH₃, $(CF_3)_2CFOCF_2CH_2CH_2S$) | $[(CF_3)_2CFOCF_2CH_2CH_2S]_2C(CH_3)(CH_3)$—$CH_2$—$CHCOOH$ |
| 6. $C_6H_{13}CH_2CH_2SH$ | $C_4H_9CH_2SH$ | (structure with $C_2H_5$, CH—CH, C, C=O, O, CH₃) | (structure with $C_2H_5$, CH₂—CH, CH₂, C=O, O, CH₃, $C_6F_{13}CH_2CH_2S$) | $C_{16}F_{16}CH_2CH_2S$—$C(CH_3)(C_2H_5)$—$CH_2CHCOOH$, $C_4F_9CH_2S$ |
| 7. $C_8F_{17}CH_2CH_2OCH_2CH_2CH_2SH$ | $C_8F_{17}CH_2CH_2OCH_2CH_2CH_2SH$ | (structure with $CH_2C_6H_5$, CH—CH, C, C=O, O, CH₃) | (structure with $CH_2C_6H_5$, CH₂—CH, CH₂, C=O, O, CH₃, $C_8F_{17}CH_2CH_2OCH_2CH_2CH_2S$) | $[C_8F_{17}CH_2CH_2OCH_2CH_2CH_2S]_2C(CH_3)(CH_2C_6H_5)$—$CH_2$—$CHCOOH$ |
| 8. $C_8F_{17}CH_2CH_2N(CH_3)CH_2CH_2SH$ | $C_8F_{17}CH_2CH_2N(CH_3)CH_2CH_2SH$ | (structure with $CH_2$, CH—CH, C, C=O, O, $CH_3CH_2$) | (structure with $CH_2$, $CH_2$—$CH_2$, C, C=O, O, $CH_3CH_2$, $C_8F_{17}CH_2CH_2N(CH_3)CH_2CH_2S$) | $[C_8F_{17}CH_2CH_2N(CH_3)CH_2CH_2S]_2C(CH_3)$—$CH_2CH_2COOH$ |
| 9. $C_6F_{13}CH_2CH_2SH$ | $C_6F_{13}CH_2CH_2SH$ | (structure with CH₃, CH—CH, C, C=O, O, CH₃) | (structure with CH₃, $CH_3CH_2$—$CH$, CH, C=O, O, $C_6F_{13}CH_2CH_2S$) | $[C_6F_{13}CH_2CH_2S]_2C(CH_2CH_3)$—$CH_2CH_2COOH$ |
| 10. $C_6F_{13}CH_2CH_2SH$ | $C_6F_{13}CH_2CH_2SH$ | (structure with CH₃, CH—CH, C=O, O, CH) | $CH_3$—$CH$—$CH$—$CH_3$, H—C, C=O, O, $C_6F_{13}CH_2CH_2S$ | $[C_6F_{13}CH_2CH_2S]_2C$—$CH$—$CHCOOH$ (with H, CH₃, CH₃) |
| 11. $C_6F_{13}CH_2CH_2SH$ | $C_6F_{13}CH_2CH_2SH$ | (structure with $C_6H_5$, CH—CH, C, C=O, O, CH₃) | (structure with $C_6H_5$, CH₂—CH, C, C=O, O, CH₃, $C_6F_{13}CH_2CH_2S$) | $[C_6F_{13}CH_2CH_2S]_2C(CH_3)(C_6H_5)$—$CH_2$—$CHCOOH$ |

What is claimed is:

1. A perfluoroalkyl-alkylthio lactone of the formula

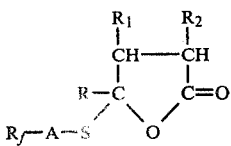

wherein $R_f$ is perfluoroalkyl of 3 to 18 carbon atoms or perfluoroalkoxyperfluoroalkyl of 3 to 18 carbon atoms, or mixtures thereof;

A is alkylene of 1 to 6 carbon atoms;

$R_1$ is hydrogen or lower alkyl;

$R_2$ is hydrogen, lower alkyl, aryl or aryl substituted lower alkyl, where aryl in each case is phenyl or phenyl substituted by lower alkyl, lower alkoxy, halo, lower alkanoyl or alkanoyloxy; and R is hydrogen or alkyl of 1 to 6 carbon atoms.

2. A compound according to claim 1, wherein $R_f$ is perfluoroalkyl of 4 to 16 carbon atoms, $R_1$ is hydrogen or methyl, and $R_2$ is hydrogen, methyl, ethyl or benzyl.

3. A compound according to claim 1, wherein A is ethylene.

4. A compound according to claim 2, wherein R is alkyl of 1 to 4 carbon atoms.

5. A compound according to claim 2, wherein R is methyl.

* * * * *